(12) United States Patent
Triel et al.

(10) Patent No.: US 10,010,697 B2
(45) Date of Patent: Jul. 3, 2018

(54) URINARY CATHETER

(71) Applicant: Coloplast A/S, Humlebaek (DK)

(72) Inventors: Egon Triel, Gilleleje (DK); Johnny Wagner, Zhuhai (CN)

(73) Assignee: Coloplast A/S, Humlebaek (DK)

( * ) Notice: Subject to any disclaimer, the term of this patent is extended or adjusted under 35 U.S.C. 154(b) by 931 days.

(21) Appl. No.: 14/249,369

(22) Filed: Apr. 10, 2014

(65) Prior Publication Data

US 2014/0221984 A1   Aug. 7, 2014

Related U.S. Application Data

(63) Continuation of application No. 13/378,577, filed as application No. PCT/DK2010/050165 on Jun. 25, 2010, now Pat. No. 8,734,427.

(30) Foreign Application Priority Data

Jun. 26, 2009   (DK) ................................ 2009 70040

(51) Int. Cl.
    *A61M 25/00*   (2006.01)

(52) U.S. Cl.
    CPC .... *A61M 25/0017* (2013.01); *A61M 25/0021* (2013.01); *A61M 25/0023* (2013.01); *A61M 25/0068* (2013.01); *A61M 25/0069* (2013.01)

(58) Field of Classification Search
    CPC .......... A61M 25/0017; A61M 25/0021; A61M 25/0023; A61M 25/0068
    See application file for complete search history.

(56) References Cited

U.S. PATENT DOCUMENTS

| 4,248,234 A | 2/1981 | Assenza et al. |
| 4,563,180 A * | 1/1986 | Jervis ................ A61M 25/0023 604/523 |

(Continued)

FOREIGN PATENT DOCUMENTS

| EP | 0384476 A1 | 8/1990 |
| EP | 0795339 A1 | 9/1997 |

(Continued)

OTHER PUBLICATIONS

The Edinburgh Medical and Surgical Journal, "Exhibiting a concise view of the latest and the most important discoveries in Medicine, Surgery and Pharmacy", 1814, vol. 10, p. 54.

(Continued)

*Primary Examiner* — Laura Bouchelle
(74) *Attorney, Agent, or Firm* — Coloplast Corp., Coloplast A/S; Nick Baumann

(57) ABSTRACT

A urinary catheter includes a tube and a tip. The tube has a tube wall defining a lumen extending between a distal tube end and a proximal tube end, with an opening formed in the tube wall. The tip extends from the proximal tube end to a closed proximal tip end. An inside diameter of the lumen increases constantly along an entire length of the tube from a first inside diameter measured at the proximal tube end to a second inside diameter measured at the distal tube end, where the first inside diameter is smaller than the second inside diameter such that the lumen is formed in a conical shape that diverges from the proximal tube end to a wider cross-sectional opening at the distal tube end.

8 Claims, 3 Drawing Sheets

(56) References Cited

U.S. PATENT DOCUMENTS

| | | | |
|---|---|---|---|
| 4,750,877 A | | 6/1988 | McFarlane |
| 2004/0193143 A1 | | 9/2004 | Sauer |
| 2005/0033237 A1 | * | 2/2005 | Fentress ............ A61M 25/0009 604/165.03 |

FOREIGN PATENT DOCUMENTS

| | | | | |
|---|---|---|---|---|
| GB | 2230702 A1 | | 10/1990 | |
| WO | 9710858 A1 | | 3/1997 | |
| WO | WO 03002179 A2 | * | 1/2003 | ............... A61F 5/44 |
| WO | 2007011287 A1 | | 1/2007 | |
| WO | 2008051647 A1 | | 5/2008 | |

OTHER PUBLICATIONS

Darke et al., "Color Atlas of Veterinary Cardiology" (Mosby), 1995.
Frados, "Plastics Engineering Handbook of the Society of the Plastics Industry, Inc.", 1976, pp. 653-654.

* cited by examiner

URINARY CATHETER

FIELD OF THE INVENTION

The present invention relates to a catheter having an outer surface, where the outer surface of the tube part, at its proximal end, has a first outer diameter that is smaller than a second outer diameter at the tube parts distal end, and the diameter of the outer surface of the tube part increases constantly along the entire length of the tube part from its proximal first outer diameter end to its distal second outer diameter.

BACKGROUND OF THE INVENTION

Urinary catheters are widely used by persons who have problems with respect to voluntary emptying of the urinary bladder or persons who need temporary assistance in emptying the urinary bladder. A wide variety of different types of urinary catheters is available to individuals or medical professionals, which are specifically designed for a specific use, such as intermittent catheters or permanent/long term catheters, such as foley catheters.

Intermittent catheters are widely used by individuals who are paralyzed, such as para- and/or tetraplegics, where the urinary bladder is emptied in regular intervals and the individuals are often capable of inserting the intermittent catheter without assistance. The use of permanent or long-term catheters is usually linked to an individual's hospital stay or at least where the individual is under regular observation of medical professionals, as permanent catheters are not well adapted for self catheterization as they are usually very flexible and have a larger diameter than intermittent catheters and thus are usually inserted by medical professionals under relatively clean or even sterile conditions.

Urinary catheters are generally known to comprise a catheter tube for providing a fluid pathway from the urinary bladder to the outside of the body, a rounded tip for smoothing the insertion of the catheter into the urinary channel and drainage eyes for facilitating the entering of urine into the catheter tube.

The most common method of producing urinary catheters, especially intermittent catheters, is to extrude the catheter tube in a plastic material and subsequently provide the catheter with a tip and drainage eyes. Catheters that are manufactured using the extrusion process have a uniform and constant diameter on both the external and the internal surface from end to end, and therefore have a constant thickness of material throughout the entire length of the catheter tube.

SUMMARY OF THE INVENTION

According to the invention, a catheter is provided comprising a tube part having a proximal end and a distal end and having a wall defining an inner lumen of the tube portion, a tip part having a proximal end and a distal end where the proximal end of the tip part is the most proximal part of the urinary catheter and the distal end of the tip part abuts the proximal end of the tube part, where the tip part extends from an outer surface of the wall of the tube part towards a central longitudinal axis of the tube part providing an uninterrupted solid material at the proximal end of the tube part, at least one through-going opening where the through-going opening is positioned in the wall of the tube part distal to the proximal end of the tube part, wherein the tube part, at its proximal end, has a first outer diameter that is smaller than a second outer diameter at the distal end of the tube part, and the outer diameter of the tube part increases constantly along the entire length of the tube part from its proximal first outer diameter end to its distal second outer diameter where the outer surface is at an angle α in relations to the central longitudinal axis of the tube part.

Within the meaning of the present invention the central longitudinal axis of the tube part is defined as an axis that extends along the radial centre of the tube part along its longitudinal axis as seen on an unbent or undistorted catheter tube. Further, the inner or outer diameter of the circular tube part may be seen as a straight line passing through a radial centre of the tube part meeting the inner or outer circumference of the tube part, respectively, seen from a sectional view perpendicular to the longitudinal axis.

Within the meaning of the present invention the term constantly increasing means that the increase is linear at a predefined ratio. That is, the diameter increases a predefined distance in a radial direction from the central axis of the tube part along a predefined length of the tube portion along its central axis. As an example, for each 1 cm of length of the tube portion along its central axis, the diameter increases 1 mm. Another definition may be that the constant increase in diameter is defined at a predefined angle from the central axis of the tube portion. On the basis of the present disclosure, any other suitable method for defining the constantly increasing term is obvious to the skilled person.

By providing a catheter having an outer surface of the tube part having at its proximal end a first outer diameter that is smaller than a second outer diameter at the tube parts distal end, the catheter is formed in a substantially conical shape, where the conical shape is directed so that the narrow end of the cone is directed towards the proximal end of the tube part and the wide end of the cone is directed towards the distal end of the tube part. Within the context of the present disclosure, it is to be understood that the proximal end of the catheter is the part which is closest to the user prior to or during insertion of the catheter and the distal part is the part of the catheter that is farthest away from the user during the insertion of the catheter. The tip of the catheter closes off the proximal end of the tube part, so that the proximal end of the tube part does not provide fluid communication with the inner lumen of the tube part.

It has been discovered that the conically shaped catheter tube provides an easier insertion of the catheter into the urethra. Even a catheter with an outer surface of a conical shape having an angle of more than 0° and less than 2° from the central longitudinal axis will improve the ease of insertion into the urethra. This is especially useful for inexperienced or new users, as it will be easier to find the urethra, without first touching the surrounding skin, with a catheter where the proximal end of the catheter has a smaller diameter than the rest of the catheter. By avoiding touching the skin surrounding the urethra with the catheter, the risk of urinary infections may be decreased.

A further advantage of a conically shaped catheter tube according to the present invention is that, during insertion of the catheter into the urethra, the catheter gradually opens up or expands the urethra in a radial direction upon the gradual insertion of the conically shaped catheter. This may reduce the risk of exerting trauma onto the soft and fragile tissue of the urethra during the insertion of the catheter, compared to a conventional catheter with a constant diameter that instantly forces the urethra to open up or expand in a radial direction to the catheters full diameter upon the passing of the catheter tip into the urethra.

In one embodiment of the present invention the tip part may be formed in such a way that the proximal part of the tip part may be rounded in the form of a substantially spherical shape. The spherical shape of the tip allows for the gradual increase in diameter of the tip part from its proximal end towards its distal end so that the tip does not have any sharp edges or sharp areas that might cause trauma to the urethra during the insertion of the catheter. The spherical tip maintains the functionality of the above-mentioned tip part in that it ensures that the proximal end of the tube part is closed, preventing fluid communication from the inner lumen via the proximal end.

In one embodiment of the present invention, the tube part may have a first inner diameter at the proximal end of the tube part that may be smaller than a second inner diameter at the distal end of the tube part. By providing the inner surface of the tube part with a first inner diameter and a second inner diameter, it is possible to reduce the size of the proximal end of the catheter considerably and thereby reduce the size of the tip part also. A catheter with a constant diameter inner surface will restrict both the minimum choice of a first outer diameter of the proximal end and subsequently restrict the choice of material thickness of the walls of the tube part. Thus, the reduction of the inner diameter at the proximal end may contribute to the choice of minimum outer diameter of the proximal end of the tube part. As an example, if the inner diameter of the tube part is made constant from the proximal end to the distal end, one of the design criteria's that will set the minimal diameter will be the required flow specifications. Hence, if the design requirements are that the fluid flow through the catheter tube is supposed to be at a predefined minimum, the constant inner diameter of the tube will also have to be predefined at a certain minimum to achieve this fluid flow.

In one embodiment of the present invention, the inner diameter of the tube part may increase constantly along the entire length of the tube part from its proximal first inner diameter to its distal second inner diameter where an inner surface of the tube part may be at an angle β in relation to the central longitudinal axis of the tube part. The constantly increasing diameter may be an advantage to some applications of a catheter according to the present disclosure, where the liquid flow of urine inside the inner lumen is even and there are no obstacles inside the inner lumen and the risk of blockages inside the inner lumen is reduced. Furthermore, a smooth inner surface may improve the flow of urine compared to an uneven surface, so that the risk of creating vortexes or uneven urine flow is minimized. The improved urine flow inside the inner lumen may result in the flow of urine out of the proximal end of the catheter being even and the risk of the urine spraying out of the proximal end of the tube part being reduced. Spraying urine is a problem for catheter users, as the spray may land on the user's clothes, the toilet seat or surrounding structures, which complicates the act of urination for e.g. a para- or tetraplegic user of a urinary catheter.

In one embodiment of the present invention, the angle α may be equal to the angle β. The angles α and β are the angles between the outer surface and the inner surface of the tube part and the central longitudinal axis of the tube part, respectively. By constructing the tube part having the angles α and β equal means that the outer surface and the inner surface are parallel along the entire length of the tube part. Thus, the walls of the tube part may have a material thickness that is constant from the proximal end of the tube part to the distal end of the tube part. The constant thickness results in the tube part having a substantially even flexibility along the length of the tube part, i.e. a first area of the tube part which is close to the proximal end of the tube part has substantially the same flexibility as a second area that is located away from the first area, such as a second area that is close to the distal end of the tube part. This means that the flexibility of the tube part, and thereby the catheter, may be chosen using either the material thickness or a combination of material choice and material thickness, as different materials may have different flexibility characteristics. With urinary catheters, it is well known that it is not hygienic to touch the insertable part of the catheter prior to insertion. Thus, having a catheter with an even flexibility along the entire length of the tube part means that, during the insertion of the catheter, the user may experience the flexibility of the proximal part during the initial insertion and use that experience to be able to assert the flexibility of the rest of the tube part, without having to touch the tube part of the catheter.

In another embodiment of the present invention, the angle α may be larger than the angle β, α>β. Constructing a tube part where the angle α of the outer surface of the tube part is larger than the angle β of the inner surface of the tube part results in a tube part where the material thickness of the walls of the tube part is not even along the entire length of the tube part. This means that an inspection of a first area close to the proximal end of the tube part and an inspection of a second area close to the distal end of the tube part will reveal that the material thickness of the wall in the first area is smaller than the material thickness of the wall in the second area. The difference in thickness between the first area and the second area results in a catheter tube where a first area is more flexible than a second area that is distal to the first area viewed along the central axis of the tube part. i.e., the proximal part of the tube part is more flexible than the distal part of the tube part. A catheter that has a tube part where the angle α is larger than the angle β may result in a catheter that is easier to insert into the urethra of a user where the urethra is either relatively narrow or relatively angled in certain areas, as the proximal part which is more flexible than the distal part may more easily be maneuvered through the angled areas. The angled or narrow areas of the urethra may e.g. be the passage of the urethra past the prostate of the user or certain areas in the pelvic area where soft tissue inflammation or the like may apply external pressure to the urethra.

In one embodiment of the present invention, the angle α may be smaller than the angle β. Constructing a tube part where the angle α of the outer surface of the tube part is smaller than the angle β of the inner surface of the tube part results in a tube part where the material thickness of the walls of the tube part is not even along the entire length of the tube part. This means that an inspection of a first area close to the proximal end of the tube part and an inspection of a second area close to the distal end of the tube part will reveal that the material thickness of the wall in the first area is larger than the material thickness of the wall in the second area. The difference in thickness between the first area and the second area results in a catheter tube where a first area is stiffer than a second area which is distal to the first area viewed along the central axis of the tube part. i.e., the proximal part of the tube part is stiffer than the distal part of the tube part. A catheter with a tube part where the angle α is smaller than the angle β may result in a catheter that may be easy to manoeuvre outside the body during insertion as the proximal end of the tube part is stiffer than the distal end of the tube part. This means that the proximal part of the catheter is less likely to kink during the insertion of the catheter. Thus, subsequent to the insertion of the tip into the urethra, the user may use the increased flexibility of the distal part to position his hand or hands into a more favourable position for inserting of the remaining part of the catheter, in case the user has difficulty in positioning his hands into the optimal position for inserting the catheter.

In one embodiment of the present invention, the angle α and/or the angle β may be larger than 0° and smaller than 3°, such as larger than 0.01° and smaller than 2.5°, such as larger than 0.05 and smaller than 2°, such as larger than 0.07° and smaller than 1.5°, such as larger than 0.1° and smaller than 1°, such as larger than 0.12° and smaller than 0.5°, such as larger than 0.13° and smaller than 0.02, such as 0.15°. The size of the angle of a and/or the angle β may be dependent on the length of the tube part, as the increase of the diameter of the tube part caused by the angles will increase along the length of the tube part. This means that a short catheter, which may be intended for the female user may have an angle that is larger than a longer catheter, which is intended for the male user.

As an example, a female catheter having a tube part which is approximately 7 cm long, having a an angle α of a size 0.15°, has an increase in diameter of approximately 0.36 mm from the proximal end towards the distal end, and a tube part having an angle of 0.3° has an increase in diameter of approximately 0.73 mm. This may be calculated using the following mathematical formula $$\frac{d}{2} = \tan\alpha \cdot \text{length}$$

where d is the diameter, α is the angle α and the length is the length of the catheter. The above-mentioned increases in diameter may be acceptable for a short catheter, such as a female catheter, while the same angle might be unacceptable for a longer catheter, such as a male catheter. A male catheter having a length of 30 cm and having an angle α of 0.3° has an increase in diameter of approximately 3.14 mm along its entire length, which for some users might be too much, whereas for other users this may not be an issue. Thus, the choice of the exact angle α and/or β may be dependent on the intended user, the length of the tube part, the material choice or a combination of the aforementioned.

According to one embodiment of the present invention, an inner diameter of the tube part may increase incrementally along the entire length of the tube part, from its proximal end to its distal end. By providing such a catheter, it is possible to adjust the material thickness of the walls of the catheter in certain predetermined areas, so that a specific part of the catheter, such as the proximal end or the proximal end proximal to the substantial middle of the tube part, has a flexibility that is more or less than the remaining parts of the tube part. By using incremental steps of increasing the diameter, it is possible to change the flexibility of the tube part abruptly, without the change in flexibility or material thickness being visible or affecting the outer surface of the tube part. The areas of the inner surface that are proximal and/or distal to the incremental step or steps may be provided in such a way that the angle or gradient of the surface in relation to the central axis of the tube part has an angle β.

In one embodiment of the present invention, the catheter may be provided with a hydrophilic surface coating providing low-friction characteristics when hydrated. By providing the catheter with a hydrophilic surface coating, it is possible to reduce the friction during insertion of the catheter into the urethra in order to minimize trauma to the urethra.

In one embodiment of the present invention, the at least one through-going opening in the wall of the tube part is provided with rounded edges. The provision of rounded edges in the at least one opening means that, during the insertion of the catheter, the risk of trauma to the urethra by sharp edges is minimized. One method of rounding the edges of the at least one opening may be seen in WO 08/104603.

The use of a cone shaped catheter according to the present invention may cause problems with regards to the at least one opening that is positioned in the wall of the tube part, in case the opening is provided with edges that are close to perpendicular to the outer or inner surface of the tube part. This means, that if the outer and/or the inner surface is provided at an angle from the central axis of the catheter tube and the edge of the opening is provided substantially perpendicular to the inner and/or outer surface, the outer edge of the opening will be angled towards the body of the user during insertion of the catheter. The proximal and side edges of the opening will probably not increase the risk of trauma to the urethra during the insertion of the catheter but there is increased risk that the distal edge of the opening might cause some trauma to the urethra. Thus, in one embodiment of the present invention, a distal edge of the at least one through-going opening in the wall of the tube part may be provided with a rounded edge.

In one embodiment of the present invention, the tube part and/or the tip part may be made of a thermoplastic material. Suitable thermoplastic materials may be materials such as polyurethane, polyvinyl chloride, polyethylene and other thermo-formable materials. The use of thermoplastic materials means that the construction or the shape of the catheter may be partly or fully provided by treating the catheter or the catheter material with heat, such as melting or by solidifying the material by cooling.

In one embodiment of the present invention, the catheter may further comprise a connector arranged at the distal end of the tube part. Further, in one embodiment, the connector may be made of the same material as the tube part and/or the tip part. The provision of a connector in the same material means that the connector may be constructed or shaped along with the rest of the catheter. A connector is usually used to handle the catheter prior and subsequent to the insertion of the catheter, as the connector is usually not inserted into the body or the urethra of the user. Thus, handling the connector using the hands will not contaminate the insertable part of the catheter. Furthermore, a connector may further be used to connect the catheter to a urine bag or to a further part of a catheter assembly, such as an extension urine drainage tube, or to a telescopic extension such as the extensions disclosed in WO 03/002179 or in WO 2008/138351.

In one embodiment of the present invention, the catheter may be injection moulded.

According to one embodiment of the present invention, a method of injecting the catheter according to the present invention is provided.

By providing a method of injection moulding the catheter according to the present invention, it is possible to mould the catheter into a cone shaped form and adjust the angle of the inner surface of the mould into any predetermined angle suitable to the user.

Another advantage of injection moulding the catheter is that it may be possible to mould the catheter with the tip so that the catheter tip and the catheter tube are moulded in a single injection cycle. It may be possible to mould the catheter in more than one cycle, using different catheter materials, and it may also be possible to mould a connector to the distal end of the catheter in one or more injection cycles, having the connector as an integral part of the catheter.

In other embodiments of the present invention, the catheter may be blow moulded, chiselled, trimmed, cut or cut to shape. Based on the teachings of this disclosure, any method suitable for obtaining a catheter according to the present invention is obvious to the skilled person.

BRIEF DESCRIPTION OF THE DRAWINGS

The invention will be explained in greater detail below, describing in example and referring to further advantages of the invention with reference to the drawing, in which.

DETAILED DESCRIPTION OF THE DRAWINGS

Figure 1:
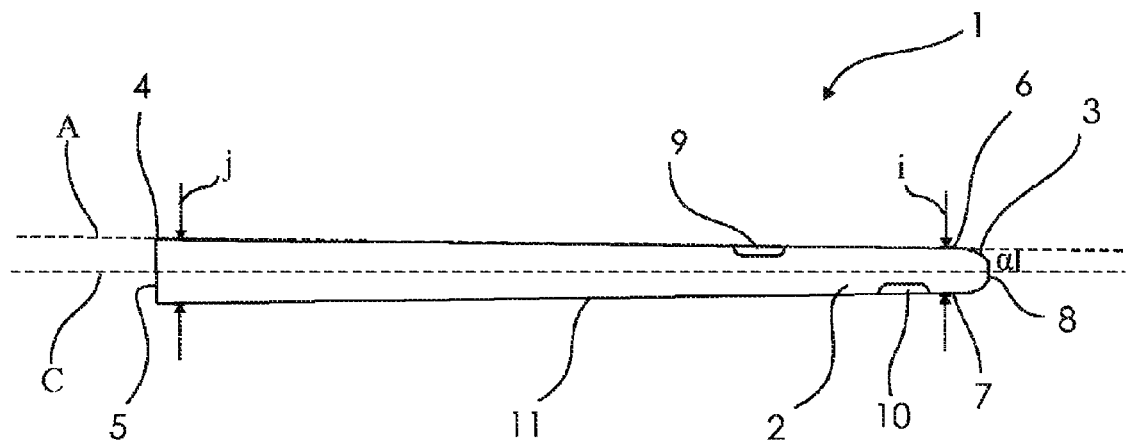
FIG. 1 shows a side view of a catheter according to the present invention showing an increase in diameter on the outer surface of the catheter, angle α.

FIG. 1 shows a side view of a catheter 1 having a catheter tube 2 defining an inner lumen and a tip 3. The catheter tube 2 has a distal end 4 that has a drainage outlet 5 and a proximal end 6, where the proximal end 6 of the catheter tube 2 abuts the tip 3 of the catheter 1. The tip 3 of the catheter 1 has a distal end 7 that abuts the proximal end 6 of the catheter tube 2 and is an integral part of the catheter 1. The tip 3 has a proximal end 8 that closes the proximal end 6 of the catheter tube 2, blocking any liquid communication through the proximal end 6 of the catheter tube 2 and the inner lumen. The proximal end 8 of the tip 3 is the most proximal part of the catheter 1 and is rounded in order to ease the insertion of the catheter 1 into the urethra of the user and to minimize the risk of causing trauma to the urethra of a user during insertion. The catheter tube 2 is provided with two drainage eyes 9,10 which are positioned distally to the proximal end 6 of the catheter tube 2 and are positioned at different positions along the central axis C of the catheter. The drainage eyes 9,10 provide liquid communication between the outside of the catheter tube 2 and the inner lumen, and subsequent to the insertion of the catheter they are used to drain urine from the urine bladder of a user.

The catheter tube 2 has an outer surface 11, where the outer surface has a first outer diameter i at the proximal end 6 of the catheter tube 2 and a second outer diameter j at the distal end 4 of the catheter tube 2, the first outer diameter i being smaller than the second outer diameter j. The increase in diameter of the outer surface 11 along the central longitudinal axis C of the catheter 1 is constant and is shown using the axis A. This means that the outer surface 11 of the catheter tube 2 is at an angle α in relation to the central longitudinal axis C of the catheter 1, resulting in a catheter 1 that may be seen as being cone shaped, having the broad section at the distal end of the catheter and the narrow section at the proximal end of the catheter.

Figure 2:
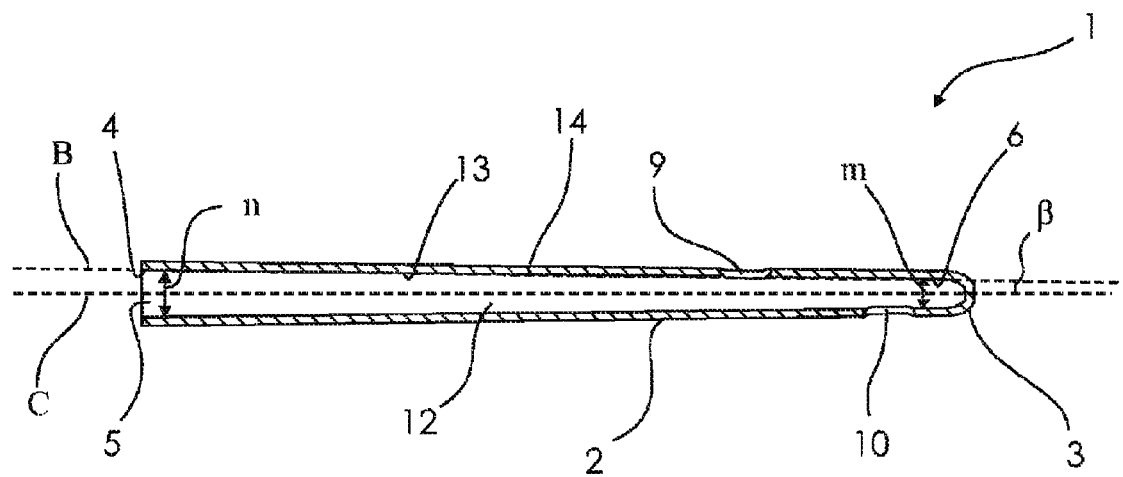
FIG. 2 shows a sectional view of a catheter taken along the central longitudinal axis of the catheter showing an increase in diameter on the inner surface of the catheter, angle β.

FIG. 2 shows a sectional view taken along the central longitudinal axis C of the catheter 1 according to the present invention. The catheter tube 2 defines an inner lumen 12 providing liquid communication from the proximal end 6 of the catheter tube 2 to the distal end 4 of the catheter tube using the drainage outlet 5. The inner surface 13 of the catheter tube 2 is the radial boundary to the inner lumen 12, and the inner surface 13 has a first inner diameter m at the proximal end 6 of the catheter tube 2 and a second inner diameter n at the distal end 4 of the catheter tube, where the first inner diameter m is smaller than the second inner diameter n. The increase in diameter of the inner surface 13 along the central longitudinal axis C of the catheter 1 is constant and is shown using the axis B. This means that the inner surface 13 of the catheter tube 2 is at an angle β in relation to the central longitudinal axis C of the catheter 1. Thus, the inner surface 13 of the catheter tube 2 may be seen as being cone shaped, similar to the outer surface 11 shown in FIG. 1.

The angles α and β, as shown in the embodiments of FIG. 1 and FIG. 2, are equal, which means that the material thickness of the catheter tube wall 14 is constant from the proximal end 6 of the catheter tube 2 to the distal end 4 of the catheter tube 2.

The catheter 1 shown in FIG. 1 or FIG. 2 may alternatively have an inner surface 13 with a first inner diameter that is equal to the second inner diameter, i.e. the diameter of the inner surface is constant from the proximal end 6 to the distal end 4 of the catheter tube.

Figure 3:
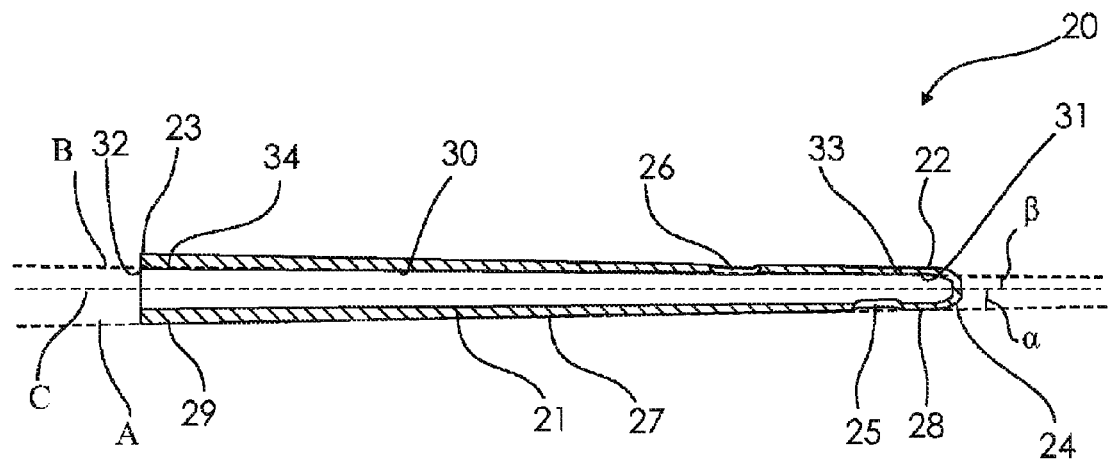
FIG. 3 shows the same having the angle α larger than the angle β.

FIG. 3 shows a catheter 20 according to the present invention, where the catheter comprises at least a tube part 21 having a proximal end 22 and a distal end 23 and a tip 24, similar to the catheter 1 of FIG. 1 and FIG. 2. The catheter is provided with drainage eyes 25,26 which are positioned distal to the proximal end 22 of the catheter tube 21.

The catheter tube 21 has an outer surface 27 having a proximal end 28 and a distal end 29 where the diameter of the proximal end 28 is smaller than the diameter of the distal end 29, and the diameter increases constantly along the central longitudinal axis C from the proximal end 28 to the distal end 29, where the increase in diameter is shown using axis A. Furthermore, the inner surface 30 of the catheter tube 21 has a proximal end 31 and a distal end 32, where the inner diameter of the proximal end 31 is smaller than the inner diameter of the distal end 32 and the diameter increases constantly along the central longitudinal axis C from the proximal end 31 to the distal end 32, where the diameter increase is shown using axis B.

The axis A and the axis B are at angles α and β, respectively, in relation to the central longitudinal axis C of the catheter 20, and in this embodiment of the present invention the angle α is larger than the angle β, i.e. the diameter increase of the outer surface 27 is larger than the diameter increase of the inner surface 30. This means that the material thickness of the proximal wall 33 of the catheter tube 21 is less than the material thickness of the distal wall 34 of the catheter tube 21 and thus the flexibility of the proximal end 22 of the catheter tube 21 is higher than the flexibility of the distal end 23 of the catheter tube, due to at least the difference in material thickness.

Figure 4:
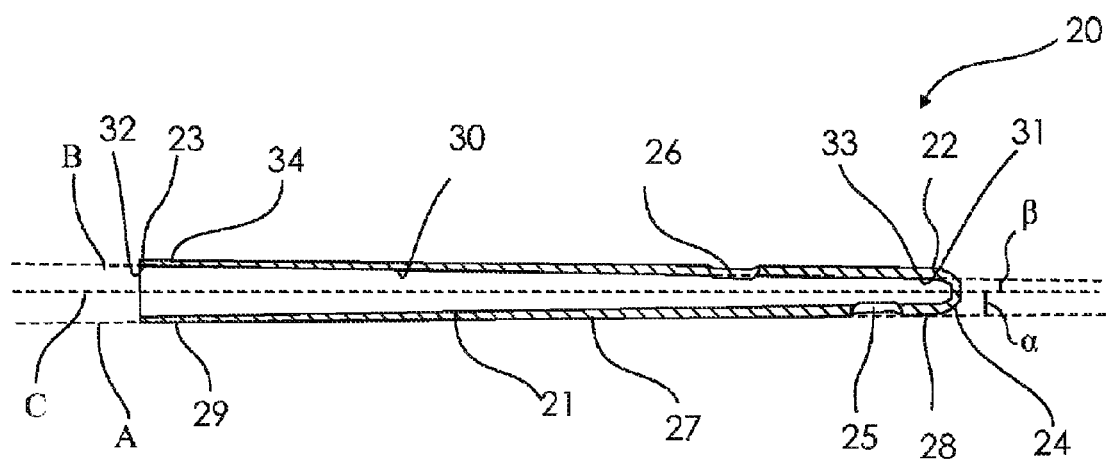
FIG. 4 shows the same having the angle α smaller than the angle β.

FIG. 4 shows another embodiment of the catheter 20 where the axis A and the axis B are at angles α and β, respectively, in relation to the central longitudinal axis C of the catheter 20, and in this embodiment of the present invention the angle α is smaller than angle β, i.e. the diameter increase of the outer surface 27 is smaller than the diameter increase of the inner surface 30. This means that the material thickness of the proximal wall 33 of the catheter tube 21 is greater than the material thickness of the distal wall 34 of the catheter tube 21 and thus the flexibility of the distal end 23 of the catheter tube 21 is higher than the flexibility of the proximal end 22, due at least to the difference in material thickness.

Figure 5:
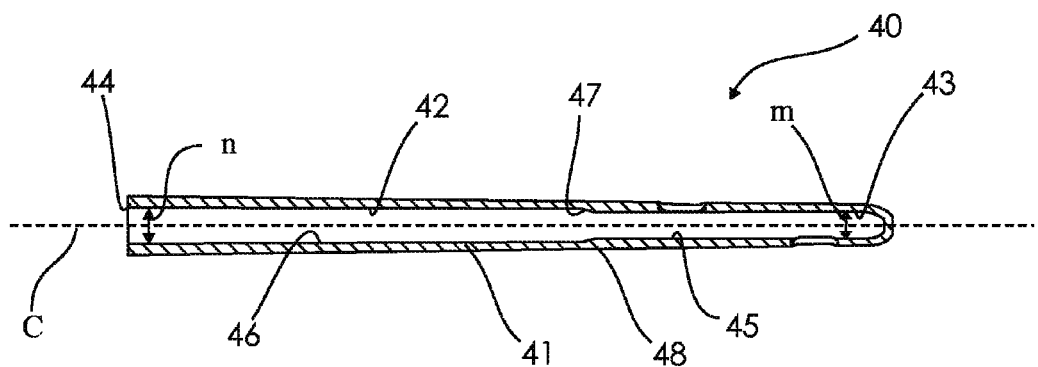
FIG. 5 shows the same having the diameter of the inner surface increased incrementally from the proximal end to the distal end, and FIGS. 6a, b and c show a catheter according to the present invention with different types of connectors.

The embodiments shown in FIG. 4 and FIG. 5 have a constant increase in diameter of the inner and the outer surfaces, which means the flexibility increases or decreases constantly along the central longitudinal axis.

FIG. 5 shows another embodiment of a catheter 40 according to the present invention, where the catheter tube 41 has an inner surface 42, where the proximal end 43 of the catheter tube 41 has a first inner diameter m and the distal end 44 of the catheter tube 41 has a second inner diameter n. The inner surface 42 has a proximal inner surface 45 and a distal inner surface 46 where the increase in diameter from the first inner diameter m to the second inner diameter n of the inner surface 42 is provided in an increment 47. This means that the flexibility difference between the proximal end and the distal end is provided in a single step, and the catheter 40 will tend to allow flexibility across the area which comprises the increment 47. This difference in flexibility and the increment 47 cannot be felt on the outer surface 48 of the catheter, as the outer surface has a constant increase in flexibility, similar to that in the embodiments of FIGS. 1-4, and bears no marks of the increment 47.

Figure 6A:
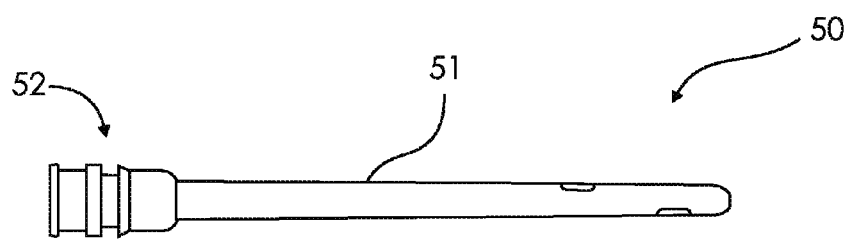
Figure 6B:
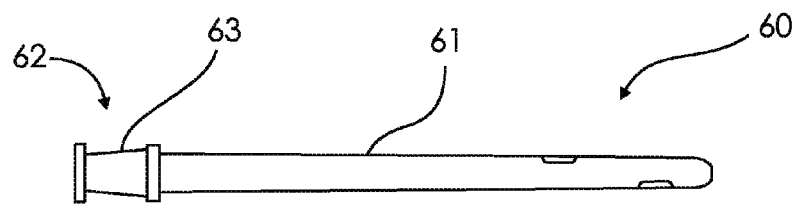

FIG. 6a shows a catheter 50 according to the present invention, where the catheter tube 51 is provided with a connector 52 in the form of a plunger used in a telescopic catheter, where the plunger provides a seal between the catheter and a catheter package, similar to that shown in WO 03/002179.

FIG. 6a shows a catheter 60 according to the present invention, where the catheter tube 61 is provided with a connector 62 in the form of a coupling used in a telescopic catheter, where the coupling has a tapered surface 63 which operates along with a locking ring in order to lock a telescopic catheter in an extended position, similar to that shown in WO 2008/138351.

Figure 6C:
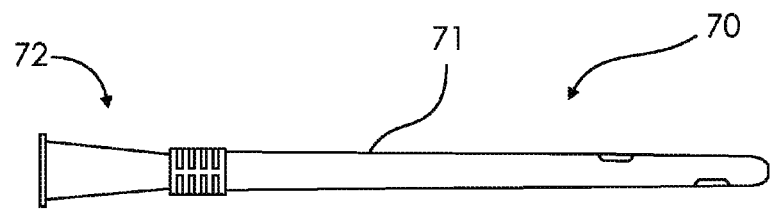

FIG. 6c shows a catheter 70 according to the present invention, where the catheter tube 71 is provided with a connector 72 in the form of a funnel shaped connector, similar to that used on the Easicath™ and the Speedicath™ products from Coloplast A/S.

The invention claimed is:

1. A urinary catheter comprising:
a tube having a tube wall defining a lumen extending between a distal tube end and a proximal tube end, with an opening formed in the tube wall distal of the proximal tube end, where the opening communicates with the lumen; and
a tip extending from the proximal tube end to a closed proximal tip end, where the closed proximal tip end forms a proximal-most end of the urinary catheter;
wherein an inside diameter of the lumen increases along a length of the tube from a first inside diameter measured at the proximal tube end to a second inside diameter measured at the distal tube end, where the first inside diameter is smaller than the second inside diameter such that the lumen is conical in shape and diverges from the proximal tube end to a wider cross-sectional opening at the distal tube end;
wherein an outside diameter of the tube increase along a length of the tube from a first outside diameter measured at the proximal tube end to a second outside diameter measured at the distal tube end, where the first outside diameter is smaller than the second outside diameter such that the tube is conical in shape and converges toward the proximal tube end; and
wherein a thickness of the tube wall measured at the proximal tube end is greater than a thickness of the tube wall measured at the distal tube end.

2. The urinary catheter of claim 1, wherein the outside diameter of the tube increases linearly along the length of the tube from the proximal tube end to the distal tube end.

3. The urinary catheter of claim 1, further comprising:
a connector attached to the tube at the distal tube end.

4. The urinary catheter of claim 1, further comprising:
a plunger connector attached to the tube at the distal tube end, where the plunger connector includes a seal between the urinary catheter and a package provided to contain the urinary catheter.

5. The urinary catheter of claim 1, further comprising:
a tapered connector attached to the tube at the distal tube end.

6. The urinary catheter of claim 1, wherein the closed proximal tip end is hemi-spherical in shape.

7. The urinary catheter of claim 1, further comprising:
a hydrophilic coating applied to an outside surface of at least the tube of the urinary catheter.

8. The urinary catheter of claim 1, wherein the opening formed in the tube wall is provided with a rounded edge.

* * * * *